(12) United States Patent
Wang et al.

(10) Patent No.: US 9,046,468 B2
(45) Date of Patent: Jun. 2, 2015

(54) SMART COATING AND METHOD FOR MANUFACTURING THE SAME

(71) Applicants: Haidou Wang, Beijing (CN); Zhiguo Xing, Beijing (CN); Binshi Xu, Beijing (CN)

(72) Inventors: Haidou Wang, Beijing (CN); Zhiguo Xing, Beijing (CN); Binshi Xu, Beijing (CN)

(73) Assignee: ACADEMY OF ARMORED FORCES ENGINEERING (CN)

(*) Notice: Subject to any disclaimer, the term of this patent is extended or adjusted under 35 U.S.C. 154(b) by 0 days.

(21) Appl. No.: 14/036,794

(22) Filed: Sep. 25, 2013

(65) Prior Publication Data
US 2014/0083196 A1 Mar. 27, 2014

(30) Foreign Application Priority Data

Sep. 26, 2012 (CN) ............ 2012 1 0364488
Sep. 26, 2012 (CN) ............ 2012 1 0364865
Sep. 26, 2012 (CN) ............ 2012 1 0364873

(51) Int. Cl.
*G01L 1/22* (2006.01)
*G01N 27/04* (2006.01)
*G01L 1/16* (2006.01)
*B82Y 30/00* (2011.01)
*G01N 29/24* (2006.01)
(Continued)

(52) U.S. Cl.
CPC ............ *G01N 27/041* (2013.01); *G01L 5/0019* (2013.01); *G01L 1/16* (2013.01); *B82Y 30/00* (2013.01); *G01N 29/24* (2013.01); *G01N 3/56* (2013.01); *G01M 99/00* (2013.01); *G01N 2203/0623* (2013.01)

(58) Field of Classification Search
CPC ................................. G01L 1/16; G01L 5/0019
USPC ..................... 73/862.041–862.046
See application file for complete search history.

(56) References Cited

U.S. PATENT DOCUMENTS 4,495,434 A * 1/1985 Diepers et al. ................ 310/338
4,504,312 A * 3/1985 Oaku et al. ....................... 75/244
(Continued)

FOREIGN PATENT DOCUMENTS

| CN | 1721854 A | 1/2006 |
| CN | 1928539 A | 3/2007 |

(Continued)

OTHER PUBLICATIONS

Piao et al. "Behavior of Rolling Contact Fatigue Crack of Plasma Sprayed Fe-based Coating" China Academic Journal Electronic Publishing House; Jan. 2011, vol. 31, No. 1, with English abstract.

*Primary Examiner* — Lisa Caputo
*Assistant Examiner* — Jonathan Dunlap
(74) *Attorney, Agent, or Firm* — Cantor Colburn LLP

(57) ABSTRACT

The present invention disclose a smart coating comprising a substrate, optionally a first insulating layer, a plurality of first sensing units, a second insulating layer, a plurality of second sensing units and optionally a wear-resistant layer, wherein the plurality of first sensing units and the plurality of second sensing units have piezoelectric effect. The smart coating can provide real-time monitoring and feedback of the worn state of the surface of a part while eliminating the need to adhere a senor. Compared with the existing sensors and substrates bound by adhesion, the smart coating provided in the present application can avoid poor adhesion between the sensor and substrate. Furthermore, damaged positions can be located precisely so as to provide more and more accurate information regarding worn state of the part surface, which is in favor of monitoring and post-stage analysis on the worn state of the surface of the part.

20 Claims, 2 Drawing Sheets

(51) Int. Cl.
*G01M 99/00* (2011.01)
*G01L 5/00* (2006.01)
*G01N 3/56* (2006.01)

(56) References Cited

U.S. PATENT DOCUMENTS 4,556,533 A * 12/1985 Oaku et al. .................. 419/11
4,634,917 A * 1/1987 Dvorsky et al. ............ 310/328
4,644,801 A * 2/1987 Kustanovich ............ 73/862.046
5,209,126 A * 5/1993 Grahn .................... 73/862.046

FOREIGN PATENT DOCUMENTS

| CN | 101561430 A | 10/2009 |
| CN | 101627484 A | 1/2010 |
| CN | 101894843 A | 11/2010 |
| CN | 102150031 A | 8/2011 |

* cited by examiner

SMART COATING AND METHOD FOR MANUFACTURING THE SAME

CROSS-REFERENCE TO RELATED APPLICATIONS

The present invention claims priority under 35 U.S.C. §119 to Chinese Application Nos. 201210364488.7 filed Sep. 26, 2012; 201210364865.7 filed Sep. 26, 2012; 201210364873.1 filed Sep. 26, 2012, the entire contents of which is incorporated herein by reference.

FIELD OF THE INVENTION

The present invention relates to the technical field of surface coating, specifically, to a smart coating and a method for manufacturing the same.

BACKGROUND OF THE INVENTION

If dynamic damage of an existing part surface on active service cannot be sensed, it is impossible to learn the worn state of the part surface.

Current part surface fatigue wear tests mostly take variation of the factors such as vibration, frictional coefficient, and temperature as a judging basis for evaluating worn state of part surfaces. When the actual value of the selected judging factors exceeds a pre-determined threshold value, it indicates failure of the part surface. Afterwards, the failed part is subjected to fracture analysis to reversely infer the mechanism of failure by experience or classical theory. However, such ex-post judgment of failure and mechanism study cannot estimate critical failed state of part surfaces. Hence, a controlling mechanism capable of dynamically monitoring and controlling failure of part surface is impossible to be established.

Smart sensing elements can real-time monitor the worn state of part surfaces, thus, it is preferred to arrange smart sensing units on part surfaces.

Piezoelectric sensor that is manufactured unitizing the piezoelectric effect of piezoelectric materials is a kind of smart sensing unit used commonly at present. In the course of applying piezoelectric sensors to mechanical facilities, it is necessary to adhere piezoelectric sensors to the facilities (or parts).

Whereas, some mechanical facilities have complicated structures or work in severe environments, which causes poor binding between the piezoelectric sensors and facilities (or parts), resulting in low detection precision of the piezoelectric sensors, or even fall-off of piezoelectric sensors.

SUMMARY OF THE INVENTION

In view of the above, the present invention provides a smart coating and a method for manufacturing the same. The method for manufacturing the smart coating can largely improve the binding strength between a sensor and a substrate of a facility, thereby avoiding poor detection precision of piezoelectric sensor or even the problem of fall-off.

For achieving the above purpose, the present invention provides the following technical solution:
a smart coating, comprising:
a substrate;
optionally a first insulating layer covering on the surface of the substrate;
a plurality of first sensing units, the plurality of first sensing units being disposed on the surface of the first insulating layer and arranged in a second direction; and the first sensing units extending in a first direction;
a second insulating layer covering on the surfaces of the plurality of first sensing units and the first insulating layer;
a plurality of second sensing units, the plurality of second sensing units being disposed on the surface of the second insulating layer and arranged in the first direction, and the second sensing units extending in the second direction; and
optionally a wear-resistant layer covering on the surfaces of the second sensing units and second insulating layer;
wherein the plurality of first sensing units and the plurality of second sensing units have piezoelectric effect.

Preferably, the first direction is perpendicular to the second direction.

Preferably, the width of the first sensing unit and the width of the second sensing unit are both varying from 2 mm to 4 mm.

Preferably, the distance between two adjacent first sensing units and the distance between two adjacent second sensing units are both 2 mm to 4 mm.

Preferably, the first insulating layer and second insulating layer are both constituted by an aluminum oxide layer or a titanium oxide layer or a composite layer of aluminum oxide and titanium oxide.

Preferably, the materials for manufacturing the first sensing unit and second sensing unit are independently selected from $PbTiO_3$ or $PbZr_{0.52}Ti_{0.48}O_3$. Still more preferably, both amorphous and crystalline materials are contained in the first sensing unit and the second sensing unit.

Preferably, the ratio of the amorphous material to the crystalline material is varying from 1:5 to 1:1 by mass, and more preferably 1:3.

Preferably, the smart coating further comprises:
a first upper electrode disposed on the edge of the upper surface of the first sensing units;
a first lower electrode disposed on the edge of the lower surface of the first sensing units;
a second upper electrode disposed on the surface of the second sensing units; and
a second lower electrode disposed on the edge of the lower surface of the second sensing units.

On some occasions particularly requiring durability, the smart coating of the present invention may further comprise a strengthening composite layer under the plurality of first sensing units.

Particularly, the strengthening composite layer comprises substantially continuous matrix and particles dispersed in the matrix. More particularly, the particles are made of $PbTiO_3$, and the matrix is a lead-lean phase formed by lead loss of $PbTiO_3$; or the particles are made of $PbZr_{0.52}Ti_{0.48}O_3$, and the matrix is a lead-lean phase formed by lead loss of $PbZr_{0.52}Ti_{0.48}O_3$.

A method for manufacturing the smart coating, comprises
optionally forming a first insulating layer on a substrate;
forming a plurality of first sensing units on the surface of the first insulating layer, the plurality of first sensing units being arranged in a second direction, and the first sensing units extending in a first direction;
forming a second insulating layer on the surfaces of the plurality of first sensing units and the first insulating layer;
forming a plurality of second sensing units on the surface of the second insulating layer, the plurality of second sensing units being arranged in the first direction, and the second sensing units extending in the second direction;

optionally forming a wear-resistant layer on the surfaces of the second sensing units and the second insulating layer; and polarizing the first sensing units and second sensing units to impart piezoelectric effect to the first sensing units and second sensing units.

Preferably, forming a first insulating layer on the surface of a substrate comprises:

forming the first insulating layer on the surface of the substrate by supersonic plasma spraying process.

Preferably, forming a second insulating layer on the surfaces of the plurality of first sensing units and the first insulating layer comprises:

forming the second insulating layer on the surfaces of the plurality of first sensing units and the first insulating layer by supersonic plasma spraying process.

Preferably, forming a plurality of first sensing units on the surface of the first insulating layer comprises:

covering a mask having the shape of a plurality of first sensing units on the surface of the first insulating layer; and forming a plurality of first sensing units on the surface of the first insulating layer by supersonic plasma spraying process.

Preferably, forming a plurality of second sensing units on the surface of the second insulating layer comprises:

covering a mask having the shape of a plurality of second sensing units on the surface of the second insulating layer; and forming a plurality of second sensing units on the surface of the second insulating layer by supersonic plasma spraying process.

Preferably, forming a plurality of first sensing units on the surface of the first insulating layer or forming a plurality of second sensing units on the surface of the second insulating layer further comprises:

cooling the substrate via a circulating cooling device during the supersonic plasma spraying process, so as to obtain both amorphous phase and crystalline phase materials. Preferably, the circulating cooling device comprises a liquid nitrogen loop-typed cooling device.

Preferably, forming a wear-resistant layer on the surfaces of the second sensing units and second insulating layer comprises:

forming a wear-resistant layer on the surfaces of the second sensing units and second insulating layer by supersonic plasma spraying process.

Preferably, the method further comprises:

forming a first upper electrode on the edge of the upper surface of the first sensing units;

forming a first lower electrode on the edge of the lower surface of the first sensing units;

forming a second upper electrode on the surface of the second sensing units;

forming a second lower electrode on the edge of the lower surface of the second sensing units; and drying.

Preferably, prior to forming a first insulating layer on the surface of a substrate, the method further comprises:

pre-treating the surface of the substrate to obtain a rough substrate surface.

On the occasions that need forming a composite strengthening layer, the aforementioned method may comprise the following steps:

forming a strengthening composite layer on the substrate or optionally the first insulating layer by supersonic plasma spraying process.

In particular, in the process of forming the strengthening composite layer by supersonic plasma spraying, the powder used for spraying comprises a first powder having an average particle size of D1 and a second powder having an average particle size of D2 at a ratio of D1 to D2 varying from 2 to 6, and the supersonic plasma spraying conditions are selected so that the first powder is melted completely and the second powder is melted partially. Especially particularly, the first powder and the second powder are independently selected from $PbTiO_3$ or $PbZr_{0.52}Ti_{0.48}O_3$. The strengthening composite layer is formed from a matrix of continuous lead-lean phase and corresponding $PbTiO_3$ or $PbZr_{0.52}Ti_{0.48}O_3$ in the form of particles dispersed in the matrix of continuous lead-lean phase.

In particular, the supersonic plasma spraying conditions are selected so that the first powder is melted completely and the second powder is melted partially. The selected spraying process conditions may comprise: 1) changing the power to change melted state; 2) changing cooling condition to change lead loss state, e.g. reducing lead loss by providing cooling means in front of the substrate during plasma spraying; and 3) changing composition of the powders to change the composition and structure of the deposition layer, e.g. providing excessive lead enabling formation of stoichiometric lead titanate/lead zirconate titanate or formation of a lead-reach phase.

A locating method based on the aforementioned smart coating, comprises:

when the wear-resistant layer is worn, the first sensing units generate first detection signals, and the second senor units generate second detection signals;

screening the first detection signals and second detection signals, and selecting the maximum first detection signal and the maximum second detection signal;

locating the damaged position in the second direction of the wear-resistant layer by the first sensing unit that generates the maximum first detection signal;

locating the damaged position in the first direction of the wear-resistant layer by the second sensing unit that generates the maximum second detection signal; and determining the damaged position of the wear-resistant layer through the damaged positions in the first direction and second directions of the wear-resistant layer.

As the plurality of first sensing units and a plurality of second sensing units of the smart coating provided in the present application have piezoelectric effect, and the surface of a part is covered with a wear-resistant layer, the plurality of first sensing units and a plurality of second sensing units can real-time monitor and feedback the worn state of the part surface (i.e. the wear-resistant layer), without need of adhering a sensor. Compared with the existing sensor and substrate bound by adhesion, the smart coating provided in the present application can avoid poor adhesion between the sensor and substrate.

Furthermore, the first sensing units extend in a first direction, and the second sensing units extend in a second direction, so when the wear-resistant layer is damaged, all of the plurality of first sensing units and the plurality of second sensing units would generate electric signals, and the electric signal generated by the first sensing unit closest to the damaged position is the strongest among the first sensing units, similarly, the electric signal generated by the second sensing unit closest to the damaged position is the strongest among the second sensing units. Moreover, the first sensing units are insulated from the second sensing units, preventing mutual interference of the electric signals generated by the first sensing units and the electric signals generated by the second sensing units. By detection of the strongest electric signals, damaged positions can be located precisely so as to provide more and more accurate information regarding worn state of the part surface, which is in favor of monitoring and post-stage analysis on the worn state of the surface of the part.

DESCRIPTION OF THE DRAWINGS

In order to illustrate examples of the present invention or the technical solutions in the prior art more clearly, the drawings needed to be used in the depiction of the examples or prior art will be simply described. Obviously, the drawings in the following description are merely some examples of the present invention, and those skilled in the art are able to obtain other drawings based thereon, without any creative work.

DETAILED EMBODIMENTS

Particular embodiments of the present invention are explained in detail with reference to the drawings so as to make the above-mentioned purpose, features and advantages of the invention more evident and pellucid, but the invention is not limited to these embodiments.

In the following depiction, many specific details are elaborated to enable sufficient understanding of the present invention. However, the invention can also be carried out by other means rather than the ones depicted herein. Those skilled n the art may make similar variations without departing the concept of the present invention, thus the invention is not limited by the following examples disclosed.

Figure 1:
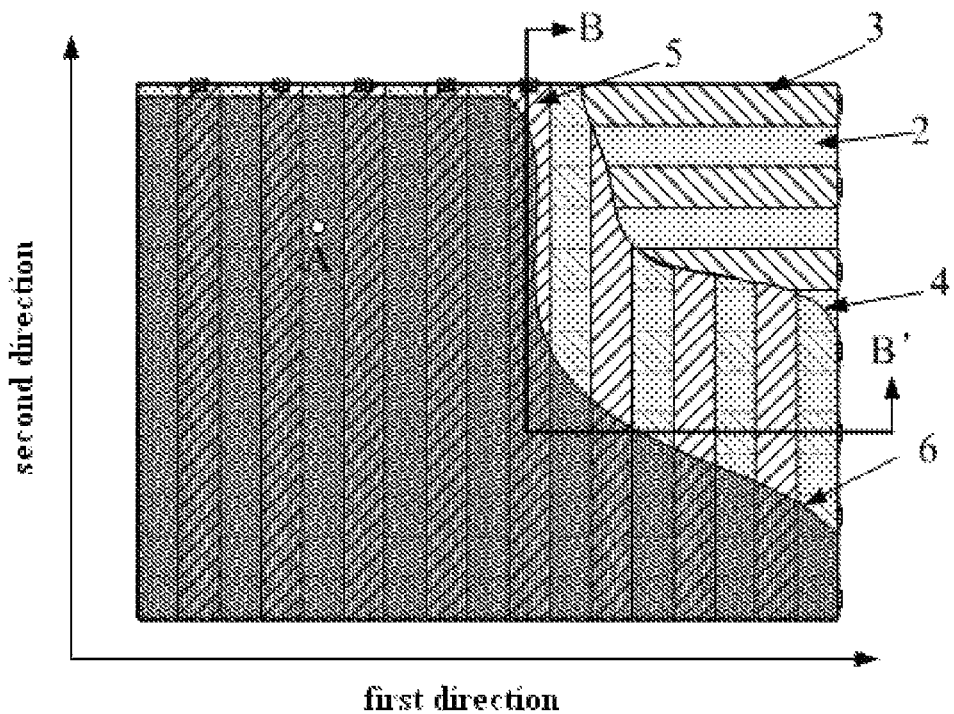
FIG. 1 is a top view of a smart coating provided in the present invention.
Figure 2:
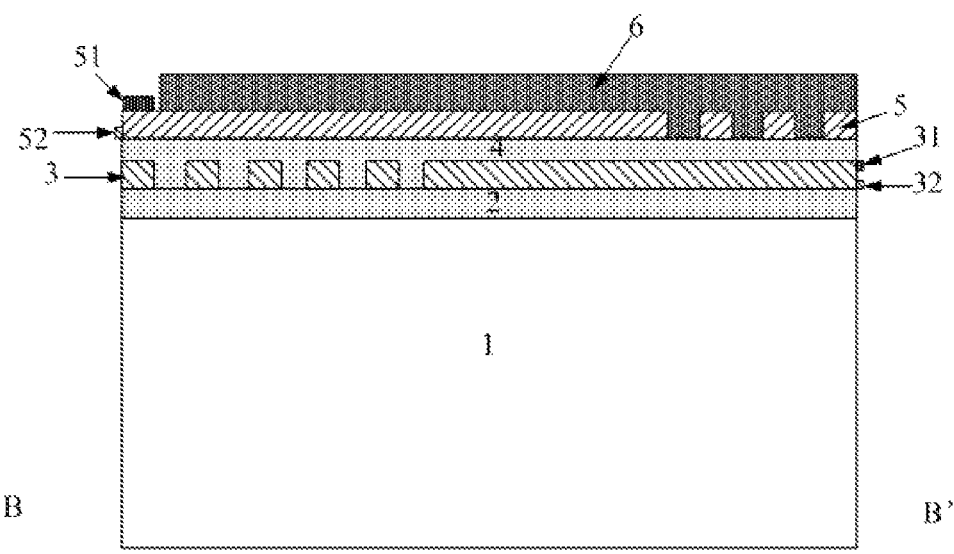
FIG. 2 is a cross section along B-B' line of a smart coating provided in the present invention.

An example of the present invention discloses a smart coating, as shown in FIG. 1 and FIG. 2, comprising:

a substrate 1 of any shape, i.e. the substrate 1 may be a part of any shape, preferably, the substrate is a metal substrate, more preferably, the substrate is a substrate made of 45# steel; and the substrate may be moving parts of a steam turbine, a compressor or a pump, or the parts such as gears, shafts, and piston pins (the parts need to undergo high frequency or flame surface quenching), or castings; or the substrate is a copper substrate or aluminum substrate to be adapted to the components used on other occasions;

a first insulating layer 2 covering on the surface of the substrate 1, the first insulating layer 2 being preferably constituted by an aluminum oxide layer or a titanium oxide layer or a composite layer of aluminum oxide and titanium oxide;

a plurality of first sensing units 3, the plurality of first sensing units 3 being disposed on the surface of the first insulating layer 2, and having a strip shape with a width of 2 mm to 4 mm, preferably 3 mm; the distance between two adjacent first sensing units is 2 mm to 4 mm, preferably 3 mm; the plurality of first sensing units 3 being arranged in a second direction and extending in a first direction that is perpendicular or approximately perpendicular to the second direction;

a second insulating layer 4 covering on the surfaces of the plurality of first sensing units 3 and the first insulating layer 2, the second insulating layer 4 being preferably constituted by an aluminum oxide layer or a titanium oxide layer or a composite layer of aluminum oxide and titanium oxide;

a plurality of second sensing units 5, the plurality of second sensing units 5 being disposed on the surface of the second insulating layer 4, and having a strip shape with a width of 2 mm to 4 mm, preferably 3 mm; the distance between two adjacent second sensing units 5 is 2 mm to 4 mm, preferably 3 mm; the plurality of second sensing units 5 being arranged in the first direction and extending in the second direction;

the first sensing units 3 and second sensing units 5 have piezoelectric effect, and the materials for the manufacture thereof are preferably piezoelectric ceramic, more preferably, $PbTiO_3$ or $BaTiO_3$ or PZT;

a wear-resistant layer 6 covering on the surfaces of the second sensing units 5 and second insulating layer 4, the wear-resistant layer is a FeCrBSi layer. The FeCrBSi alloy has low price, high binding degree with the second sensing units 5 and second insulating layer 4, and good wear resistance, so using the FeCrBSi alloy as a material for manufacturing the wear-resistant layer 6 may further increase the wear resistance of part surfaces and prevent fall-off.

As the plurality of first sensing units 3 and a plurality of second sensing units 5 of the smart coating provided in the examples of the present application have piezoelectric effect, and the surface of a part is covered with a wear-resistant layer, the worn state of the part surface (i.e. the wear-resistant layer 6) can be monitored and feedback in real time, without need of adhering a sensor. Compared with the existing sensor and substrate bound by adhesion, the smart coating provided in the present application can avoid poor adhesion between the sensor and substrate.

In addition, in the case of forming the first sensing units 3 or the second sensing units 5 on the surface of the insulating layers by supersonic plasma spraying process, the powders for spraying are allowed to have a relatively large cooling rate when depositing on the substrate by cooling the substrate, thus a partially amorphous coating is formed. Surprisingly, the applicant has discovered the resultant partially amorphous coating can further enhance the cohesion of the coating. Do not wish to be bound by the theory, the applicants believes that during the formation of the amorphous coating, the powders for spraying are cooled at a super high cooling state from a melted state, and the melt is coagulated prior to nucleation and crystallization, thereby the original state in which atoms are arranged disorderly in a liquid is maintained. This state in which atoms are arranged disorderly in a liquid improves the wetting capability of the coating to underlying layer, increasing the binding strength between the coating and the underlying layer.

Furthermore, the first sensing units 3 extend in a first direction, and the second sensing units 5 extend in a second direction, thus the first and second sensing units intersect with each other to form a grid. When the wear-resistant layer 6 is damaged, all of the plurality of first sensing units 3 and the plurality of second sensing units 5 would generate electric signals, and the electric signal generated by the first sensing unit 3 closest to the damaged position is the strongest among the first sensing units, similarly, the electric signal generated by the second sensing unit 5 closest to the damaged position is the strongest among the second sensing units. The first sensing units 3 are insulated from the second sensing units 5, preventing mutual interference of the electric signals generated by the first sensing units 3 and the electric signals generated by the second sensing units 5. By detection of the strongest electric signals, damaged positions can be located precisely so as to provide more and more accurate information of worn state of the part surface, which is in favor of monitoring and post-stage analysis on the worn state of the surface of the part.

Moreover, a first insulating layer 2 that is disposed between the plurality of first sensing units 3 and substrate 1 can prevent the electric signals generated by the plurality of first sensing units 3 from flowing into the substrate 1, thereby avoiding loss of the electric signals and increasing sensitivity of damage detection.

It follows that, when wear damage or micro-fracture of the coating (wear-resistant layer 6) on part surface are collected, the electric current generated by the smart coating can be taken as a characteristic signal to complete judgment of critical failure of the coating. Consequently, the mode of judging the state of a coating on a part surface is a multi-choice type continuous judging mode of "complete . . . relatively complete . . . unfailed . . . critical failure . . . failed", by which the failure evolution process of a coating on a part surface can be grasped in real time, on line and dynamically. Furthermore, worn positions can be located precisely so as to provide more and more accurate information of worn state of the part surface, which is in favor of monitoring and post-stage analysis on the worn state of the surface of the part.

It should be indicated that, for the first sensing units 3 and the second sensing units 5, a smaller width and a smaller spacing can increase the locating precision of the smart coating. Hence, the width and spacing of the sensing units can be altered correspondingly according to different requirements. Alternatively, the shapes of the first sensing units 3 and the second sensing units 5 are changed to extend the applicable scope thereof.

In addition, the smart coating further comprises:
a first upper electrode 31 disposed on the edge of the upper surface of the first sensing units 3, and a first lower electrode 32 disposed on the edge of the lower surface of the first sensing units 3, wherein the first upper electrode 31 and first lower electrode 32 are lead-out electrodes for the electric current that is generated by the first sensing units 3 due to coating damage; and
a second upper electrode 51 disposed on the surface of the second sensing units 5, and a second lower electrode 52 disposed on the edge of the lower surface of the second sensing units 5, wherein the second upper electrode 51 and second lower electrode 52 are lead-out electrodes for the electric current that is generated by the second sensing units 5 due to coating damage.

Besides, the first upper electrode 31, first lower electrode 32, second upper electrode 51 and second lower electrode 52 further need connecting leads to guide the electric current out.

Preferably, the first upper electrode 31, first lower electrode 32, second upper electrode 51 and second lower electrode 52 are all gold electrodes to improve electric conductivity and reduce loss of electric current. Moreover, the first upper electrode 31, first lower electrode 32, second upper electrode 51 and second lower electrode 52 are all arranged at the non-worn positions of the coating so as to avoid the influence on electrodes caused by wearing of the coating on the part surface.

Figure 3:
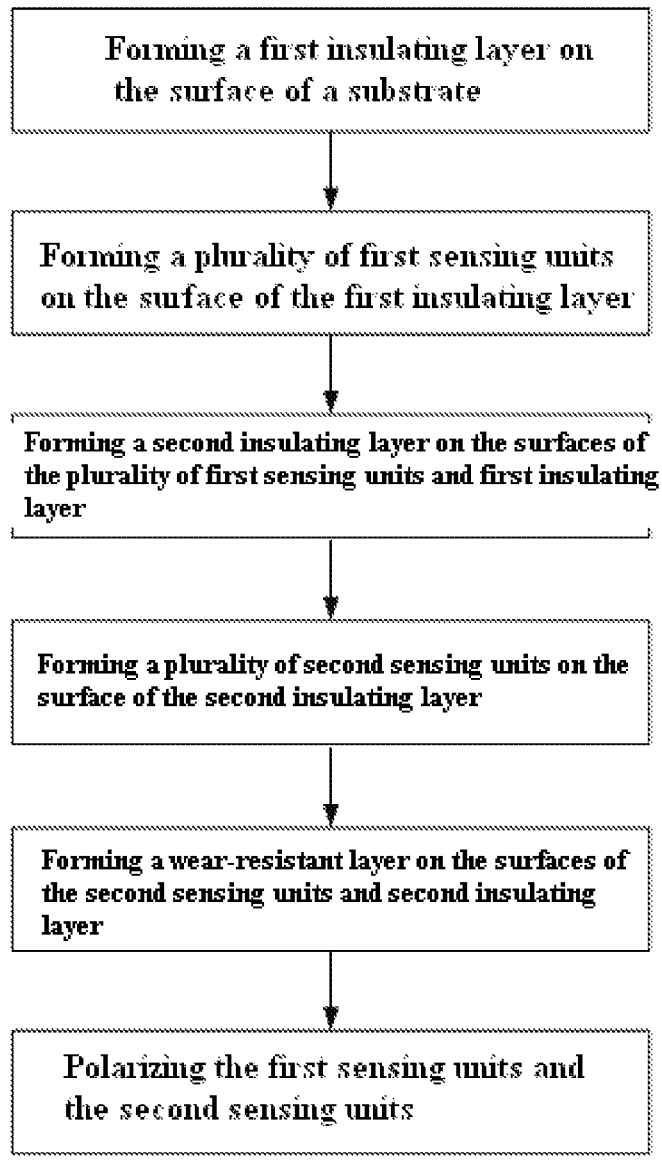
FIG. 3 is a schematic flow chart of a method for manufacturing a smart coating provided in the present invention.

Another example of the present invention discloses a method of manufacturing a smart coating, as shown in FIG. 3, comprising:
forming a first insulating layer on a substrate, wherein the substrate is a substrate of any shape, i.e. the substrate may be a part of any shape, preferably, the substrate is a metal substrate, more preferably, the substrate is a substrate made of 45# steel; and the substrate may be moving parts of a steam turbine, a compressor or a pump, or the parts such as gears, shafts, and piston pins (the parts need to undergo high frequency or flame surface quenching), or castings; or the substrate is a copper substrate or aluminum substrate to be adapted to the components used on other occasions;
forming a plurality of first sensing units on the surface of the first insulating layer, the plurality of first sensing units being arranged in a second direction, and the first sensing units extending in a first direction;
forming a second insulating layer on the surfaces of the plurality of first sensing units and the first insulating layer;
forming a plurality of second sensing units on the surface of the second insulating layer, the plurality of second sensing units being arranged in the first direction and the second sensing units extending in the second direction;
forming a wear-resistant layer on the surfaces of the second sensing units and the second insulating layer; and
polarizing the first sensing units and second sensing units to impart piezoelectric effect to the first sensing units and second sensing units, thereby completing the manufacture of the smart coating.

Since the first sensing units and second sensing units have piezoelectric effect, the sensing layer can generate electric signals to the damage on part surface, and therefore the resultant smart coating is provided with the function of a piezoelectric sensor and capable of monitoring and feedback the worn state of the part surface (i.e. the wear-resistant layer) in real time, without need of adhering a sensor. Compared with the existing sensor and substrate bound by adhesion, the smart coating provided in the present application can avoid poor adhesion between the sensor and substrate.

Furthermore, the first sensing units extend in a first direction, and the second sensing units extend in a second direction, so when the wear-resistant layer is damaged, all of the plurality of first sensing units and the plurality of second sensing units would generate electric signals. The electric signal generated by the first sensing unit closest to the damaged position is the strongest among the first sensing units. Similarly, the electric signal generated by the second sensing unit closest to the damaged position is the strongest among the second sensing units. The first sensing units is insulated from the second sensing units, preventing mutual interference of the electric signals generated by the first sensing units and the electric signals generated by the second sensing units. By detection of the strongest electric signals, damaged positions can be located precisely so as to provide more and more accurate information of worn state of the part surface, which is in favor of monitoring and post-stage analysis on the worn state of the surface of the part.

Moreover, the insulating layer that is disposed between the plurality of first sensing units and substrate can prevent the electric signals generated by the plurality of first sensing units from flowing into the substrate, thereby avoiding loss of the electric signals and increasing sensitivity of damage detection.

It follows that, when wear damage or micro-fracture of the coating (wear-resistant layer) on part surface are collected, the electric current generated by the smart coating can be taken as a characteristic signal to complete judgment of critical failure of the coating. Consequently, the mode of judging the state of a coating on a part surface is a multi-choice type continuous judging mode of "complete . . . relatively complete . . . unfailed . . . critical failure . . . failed", by which the failure evolution process of a coating on a part surface can be grasped in real time, on line and dynamically. Furthermore, worn positions can be located precisely so as to provide more and more accurate information of worn state of the part surface, which is in favor of monitoring and post-stage analysis on the worn state of the surface of the part.

Another example of the present invention discloses another method of manufacturing a smart coating, comprising:

forming a first insulating layer on the surface of a metal substrate by supersonic plasma spraying process, wherein the material for manufacturing the first insulating layer is aluminum oxide, titanium oxide or composite of aluminum oxide and titanium oxide.

Specifically, in the present example, the supersonic plasma spraying process for forming the first insulating layer is carried out at conditions of:

a spraying voltage of 110V to 130V, preferably, 120V; a spraying current of 370 A to 400 A, preferably, 385 A; a spraying power of 30 kW to 50 kW, preferably, 40 kW; and a spraying distance of 100 mm to 120 mm, preferably, 110 mm.

Then, a mask having the shape of a plurality of first sensing units is covered on the surface of the first insulating layer, and a plurality of first sensing units are formed on the surface of the first insulating layer by supersonic plasma spraying process, wherein the plurality of first sensing units are arranged in a second direction, and the first sensing units extend in a first direction.

In the present example, the manufacture material of the first sensing units is piezoelectric ceramic, preferably, $PbTiO_3$. $PbTiO_3$ is sprayed on the surface of the first insulating layer by supersonic plasma spraying process, and finally form the first sensing units at the positions uncovered by the mask, with the first insulating layer exposed at the positions covered by the mask.

The supersonic plasma spraying process for forming the plurality of first sensing units is carried out at conditions of:

a spraying voltage of 110V to 130V, preferably, 120V; a spraying current of 350 A to 380 A, preferably, 365 A; a spraying power of 35 kW to 55 kW, preferably, 45 kW; and a spraying distance of 90 mm to 110 mm, preferably, 100 mm.

Thereafter, a second insulating layer is formed on the surfaces of the plurality of first sensing units and the first insulating layer by supersonic plasma spraying process, wherein the material for manufacturing the second insulating layer is aluminum oxide, titanium oxide or composite of aluminum oxide and titanium oxide.

The same as the manufacture process of the first insulating layer, in the present example, the supersonic plasma spraying process for forming the second insulating layer is carried out at conditions of:

a spraying voltage of 110V to 130V, preferably, 120V; a spraying current of 370 A to 400 A, preferably, 385 A; a spraying power of 30 kW to 50 kW, preferably, 40 kW; and a spraying distance of 100 mm to 120 mm, preferably, 110 mm.

A mask having the shape of a plurality of second sensing units is then covered on the surface of the second insulating layer; and a plurality of second sensing units are formed on the surface of the second insulating layer by supersonic plasma spraying process, wherein the plurality of second sensing units are arranged in the first direction, and the second sensing units extend in the second direction.

In the present example, the manufacture material of the second sensing units is piezoelectric ceramic, preferably, $PbTiO_3$. $PbTiO_3$ is sprayed on the surface of the second insulating layer by supersonic plasma spraying process, and finally form the second sensing units at the positions uncovered by the mask, with the second insulating layer exposed at the positions covered by the mask.

The supersonic plasma spraying process for forming the plurality of second sensing units is carried out at conditions of:

a spraying voltage of 110V to 130V, preferably, 120V; a spraying current of 350 A to 380 A, preferably, 365 A; a spraying power of 35 kW to 55 kW, preferably, 45 kW; and a spraying distance of 90 mm to 110 mm, preferably, 100 mm.

In addition, the first sensing units and second sensing units may also be formed on the surfaces of the insulating layers by chemical vapor deposition, wherein the deposition temperature is 900° C. to 1150° C., preferably 1000° C.; the deposition time is 4 h to 8 h, preferably 6 h; and the deposition environmental pressure is 6 KPa to 15 KPa, preferably 10 KPa.

Then, a wear-resistant layer is formed on the surfaces of the second sensing units and the second insulating layer by supersonic plasma spraying process.

The spraying process for forming the wear-resistant layer is carried out at conditions of:

a spraying voltage of 110V to 130V, preferably, 120V; a spraying current of 410 A to 430 A, preferably, 420 A; a spraying power of 40 kW to 55 kW, preferably, 48 kW; and a spraying distance of 90 mm to 100 mm, preferably, 95 mm.

The FeCrBSi alloy has low price and good wear resistance, so using the FeCrBSi alloy as a material for manufacturing the wear-resistant layer may further improve the wear resistance of part surfaces and prevent fall-off.

Lastly, the first sensing units and second sensing units are subjected to polarizing treatment so as to impart piezoelectric effect to the first sensing units and second sensing units, thereby completing the manufacture of the smart coating.

Specifically, the first sensing units and second sensing units are placed in a polarizing electric field to perform polarization at a polarizing temperature of 180° C. to 200° C., preferably 190° C.; and a polarizing electric field intensity of 2.4 KV/mm to 2.6 KV/mm, preferably 2.5 KV/mm, for not less than 15 min, preferably, 15 min to 20 min, more preferably, 18 min.

It needs to be indicated that, supersonic plasma spraying process, as one of thermal spraying, is an important process for the manufacture of surface coatings. In the course of supersonic plasma spraying process, a plasma jet with a high temperature that can heat various spraying materials to molten state is generated, so that not only high-quality metal or alloy coatings but also high-melting-point ceramic and cermet coatings can be manufactured, thereby greatly improving the wear resistance of coatings.

Since the first sensing units and second sensing units have piezoelectric effect, the sensing layer can generate electric signals to the damage on part surface, and therefore the resultant smart coating is provided with the function of a piezoelectric sensor and capable of monitoring and feedback the worn state of the part surface (i.e. the wear-resistant layer) in real time, without need of adhering a sensor. Compared with the existing sensor and substrate bound by adhesion, the smart coating provided in the present application can avoid poor adhesion between the sensor and substrate.

Furthermore, the first sensing units extend in a first direction, and the second sensing units extend in a second direction. When the wear-resistant layer is damaged, all of the plurality of first sensing units and the plurality of second sensing units would generate electric signals, and the electric signal generated by the first sensing unit closest to the damaged position is the strongest among the first sensing units. Similarly, the electric signal generated by the second sensing unit closest to the damaged position is the strongest among the second sensing units. The first sensing units are insulated from the second sensing units, preventing mutual interference of the electric signals generated by the first sensing units and the electric signals generated by the second sensing units. By detection of the strongest electric signals, damaged positions can be located precisely so as to provide more and more accurate information of worn state of the part surface, which is in favor of monitoring and post-stage analysis on the worn state of the surface of the part.

Moreover, the insulating layer that is disposed between the plurality of first sensing units and substrate can prevent the electric signals generated by the plurality of first sensing units from flowing into the substrate, thereby avoiding loss of the electric signals and increasing sensitivity of damage detection.

It follows that, when wear damage or micro-fracture of the coating (wear-resistant layer) on part surface are collected, the electric current generated by the smart coating can be taken as a characteristic signal to complete judgment of critical failure of the coating. Consequently, the mode of judging the state of a coating on a part surface is a multi-choice type continuous judging mode of "complete . . . relatively complete . . . unfailed . . . critical failure . . . failed", by which the failure evolution process of a coating on a part surface can be grasped in real time, on line and dynamically. Furthermore, worn positions can be located precisely so as to provide more and more accurate information of worn state of the part surface, which is in favor of monitoring and post-stage analysis on the worn state of the surface of the part.

Another example of the present invention discloses another method of manufacturing a smart coating, comprising:
    forming a first insulating layer on a substrate;
    forming a plurality of first sensing units on the surface of the first insulating layer, the plurality of first sensing units being arranged in a second direction, and the first sensing units extending in a first direction;
    forming a second insulating layer on the surfaces of the plurality of first sensing units and the first insulating layer;
    forming a plurality of second sensing units on the surface of the second insulating layer, the plurality of second sensing units being arranged in the first direction and the second sensing units extending in the second direction;
    forming a wear-resistant layer on the surfaces of the second sensing units and the second insulating layer;
    forming a first upper electrode on the edge of the upper surface of the first sensing units, and forming a first lower electrode on the edge of the lower surface of the first sensing units, wherein the first upper electrode and first lower electrode are lead-out electrodes for the electric current that is generated by the first sensing units due to coating damage;
    forming a second upper electrode on the surface of the second sensing units, and forming a second lower electrode on the edge of the lower surface of the second sensing units, wherein the second upper electrode and second lower electrode constitute lead-out electrodes for the electric current that is generated by the second sensing units due to coating damage;
    drying, wherein the drying is carried out at a drying temperature is 120° C. or more, preferably, 120° C. to 150° C., more preferably, 130° C. for a time of 15 min or more, preferably, 20 min; and
    polarizing the first sensing units and second sensing units to impart piezoelectric effect to the first sensing units and second sensing units.

The electric currents generated by the first sensing units and second sensing units are small, thus the first upper electrode, first lower electrode, second upper electrode and second lower electrode are all preferably gold electrodes to improve electric conductivity and reduce loss of electric current. The first upper electrode, first lower electrode, second upper electrode and second lower electrode are formed by coating process. For the purpose of more uniform thickness of the gold electrode, coating by three times is preferred for forming the gold electrode.

There is a need to explain that, the first upper electrode, first lower electrode, second upper electrode and second lower electrode may employ silver electrodes or aluminum electrodes according to practical requirements, without any limitation to the specific materials. The present invention uses gold electrodes in order to achieve a better electric conductivity. Moreover, the first upper electrode, first lower electrode, second upper electrode and second lower electrode are all arranged at the non-worn positions of the coating to avoid the influence on electrodes caused by wear of the coating on the part surface.

Another example of the present invention discloses another method of manufacturing a smart coating, comprising:
    providing a substrate and pre-treating the surface of the substrate to obtain a rough substrate surface, specifically, the surface of the substrate is treated by sand blasting process, in which brown corundum with particle size of 15 mesh to 30 mesh, preferably, 16 mesh, is used as sand; sand blasting pressure is 0.5 MPa to 1 Mpa, preferably, 0.7 MPa; sand blasting angle is 30° to 60°, preferably 45°; and the sand blasting distance is 130 mm to 160 mm, preferably, 145 mm;
    forming a first insulating layer on a substrate, the degree of binding between the first insulating layer and substrate being higher due to increased roughness of the substrate by the pre-treatment process;
    forming a plurality of first sensing units on the surface of the first insulating layer, the plurality of first sensing units being arranged in a second direction, and the first sensing units extending in a first direction;
    forming a second insulating layer on the surfaces of the plurality of first sensing units and the first insulating layer;
    forming a plurality of second sensing units on the surface of the second insulating layer, the plurality of second sensing units being arranged in the first direction, and the second sensing units extending in the second direction;
    forming a wear-resistant layer on the surfaces of the second sensing units and second insulating layer;
    forming a first upper electrode on the edge of the upper surface of the first sensing units, and forming a first lower electrode on the edge of the lower surface of the first sensing units, wherein the first upper electrode and first lower electrode are lead-out electrodes for the electric current that is generated by the first sensing units due to coating damage;
    forming a second upper electrode on the surface of the second sensing units, and forming a second lower electrode on the edge of the lower surface of the second sensing units, wherein the second upper electrode and second lower electrode are lead-out electrodes for the electric current that is generated by the second sensing units due to coating damage;

drying at a temperature of 120° C. for 20 min; and polarizing the first sensing units and second sensing units to impart piezoelectric effect to the first sensing units and second sensing units.

A further example of the present invention discloses another method of manufacturing a smart coating, comprising:

provided a substrate and quenching the substrate to improve the hardness thereof, thereby to achieve a hardness of around HRC55;

sand blasting the surface of the substrate with brown corundum to make the substrate surface possess a certain roughness;

independently granulating aluminum oxide powder, titanium oxide powder, $PbTiO_3$ powder and FeCrBSi powder to form granulates of aluminum oxide powder, titanium oxide powder, $PbTiO_3$ powder and FeCrBSi powder all having uniform particle size reaching 40 μm to 70 μm;

spraying aluminum oxide and titanium oxide on the surface of the substrate to form a first insulating layer, specifically, the aluminum oxide power and titanium oxide powder granulated independently are charged into a powder feeder, powder feed amount is adjusted to 30 g/min, and the substrate surface subjected to sand blasting is sprayed at a spraying current of 378 A, a spraying voltage of 105V, a spraying power of 42.6 kW, and a spraying distance of 110 mm, with argon gas at a flow rate of 3.0 m³/h as spraying main gas and hydrogen gas at a flow rate of 0.25 m³/h as secondary gas, to form an insulating layer with a thickness of 60 μm;

covering a mask having the shape of first sensing units on the surface of the first insulating layer, charging the $PbTiO_3$ powder granulated independently to a powder feeder, adjusting the powder feed amount to 30 g/min, and spraying on the substrate surface formed with the first insulating layer at a spraying current of 360 A, a spraying voltage of 120V, a spraying power of 43.2 kW, and a spraying distance of 100 mm, with argon gas at a flow rate of 3.2 m³/h as spraying main gas and hydrogen gas at a flow rate of 0.3 m³/h as secondary gas, to form the first sensing units with a thickness of 100 μm;

spraying aluminum oxide and titanium oxide on the surfaces of the first sensing units and first insulating layer to form a second insulating layer, which process is the same as the spraying process of the first insulating layer;

covering a mask having the shape of second sensing units on the surface of the second insulating layer, charging the $PbTiO_3$ powder granulated independently to a powder feeder, adjusting the powder feed amount to 30 g/min, and spraying on the substrate surface formed with the second insulating layer at a spraying current of 360 A, a spraying voltage of 120V, a spraying power of 43.2 kW, and a spraying distance of 100 mm, with argon gas at a flow rate of 3.2 m³/h as spraying main gas and hydrogen gas at a flow rate of 0.3 m³/h as secondary gas, to form the second sensing units with a thickness of 100 μm;

spraying a FeCrBSi alloy wear-resistant layer on the surfaces of the seconds sensing units and the second insulating layer, specifically, the FeCrBSi powder granulated independently are charged into a powder feeder, powder feed amount is adjusted to 60 g/min, and spraying is carried out at a spraying current of 420 A, a spraying voltage of 120V, a spraying power of 50.9 kW, and a spraying distance of 100 mm, with argon gas at a flow rate of 2.8 m³/h as spraying main gas and hydrogen gas at a flow rate of 0.4 m³/h as secondary gas, to form wear-resistant layer with a thickness of 300 μm;

checking after spraying is finished to remove the defects such as burrs at the edge and uncleanness, then checking with a megohm meter one by one to eliminate the products having an excessively small resistance, so as to ensure that the first sensing units and second sensing units can achieve a standard degree of polarization;

filtering or replacing insulating oil to guarantee cleanness of polarizing tank, polarizing oil and polarizing plate, adjusting the pointer of a moving coil type temperature regulator to the temperature for polarization, increasing oil temperature to the required polarization temperature by heating the polarizing tank, adjusting a time relay to the required polarization time (15 min to 30 min), placing the substrate that is formed with the first sensing units and second sensing units and preheated according to the polarization temperature between a positive electrode and a negative electrode of the polarizing tank, and closing the door of the polarizing chamber; turning on the low-voltage power supply switch of the rectifier portion, preheating for several minutes, and turning on the high-voltage switch, at the same time, the time relay beginning timing; slowly increasing the voltage value between the positive and negative electrodes from 2500V to a preset numerical value (5000V) with every 100V or 200V as a grade, the high-voltage switch automatically closing once the polarization time is reached, thereby the first sensing units and second sensing units possessing piezoelectric effect after polarization is finished and the manufacture of a smart coating being completed.

Another example of the present application discloses a locating method based on the smart coating of any of the above-mentioned examples, which comprises:

when the wear-resistant layer is worn, the plurality of first sensing units generate a plurality of first detection signals, and the plurality of second senor units generate a plurality of second detection signals.

As shown in FIG. 1, when wear damage with point A as a center occurs, the first sensing units 3 and the second sensing units 5 that are adjacent to the point A are stressed by tearing or pulling of the coating (the wear-resistant layer 6), and the closer to the point A, the larger the stress on the sensing unit. Based on the characteristics of piezoelectric ceramic per se, all of the first sensing units 3 and second sensing units 5 would generate piezoelectric currents, and the sensing unit closer to the point A will generate a larger piezoelectric current. The piezoelectric currents generated by all of the first sensing units 3 and second sensing units 5 are taken as detection signals, correspondingly, the plurality of piezoelectric currents generated by the plurality of first sensing units 3 serve as a plurality of first detection signals, and the plurality of piezoelectric currents generated by the plurality of second sensing units 5 serve as a plurality of second detection signals. The plurality of first detection signals and the plurality of second detection signals are screened to select the maximum first detection signal and maximum second detection signal.

As the sensing unit closer to the point A will generate a larger piezoelectric current, the first sensing unit 3 closest to the point A would generate the maximum first detection signal, and the second sensing unit 5 closest to the point A would generate the maximum second detection signal. Therefore, the other way round, the specific position of point A can be determined by the first sensing unit 3 that generates the maximum first detection signal and the second sensing unit 5 that generates the maximum second detection signal.

Specifically, the first direction and second direction can be put in a direct coordinate system, with the first direction as X axis direction in the coordinate system and the second direction as Y axis direction in the coordinate system. The first sensing unit 3 that generates the maximum first detection signal can locate the damage of the wear-resistant layer in the second direction, i.e. Y-coordinate of point A. The second sensing unit 5 that generates the maximum second detection signal locates the damage of the wear-resistant layer in the first direction, i.e. X-coordinate of point A. The position of the damage in the wear-resistant layer can be determined through the positions in the first and second directions of the damage of the wear-resistant layer (X and Y coordinates of point A), so as to provide more and more accurate information of worn state of the part surface, which is in favor of monitoring and post-stage analysis on the worn state of the surface of the part.

Furthermore, it can be seen from FIG. 1 that, each first sensing unit 3 of the smart coating is insulated from each other, thus the first detection signal generated by a certain first sensing unit 3 does not influence other first sensing units 3. Similarly, the second detection signal generated by a certain second sensing unit 5 does not influence other second sensing units 5. Moreover, the first sensing units 3 are insulated from the second sensing unit 5, which avoids mutual influence between the first detection signals and second detection signals. Consequently, the worn state of the substrate surface can be detected more precisely.

In the aforementioned smart coatings and manufacture methods, some examples of the present invention further involve formation of an additional strengthening composite layer. In some applications of smart coating sensors, durability is of paramount importance. For example, in a part where fatigue failure predominates, the durability of a smart coating sensor attached to the surface of the part is expected to be at least sufficient to ensure good attachment of the sensor on the part before failure of the part. The sensor layer is generally a ceramic layer such as a lead titanate ceramic layer, which has large brittleness and is prone to cracking and low in the resistance to cracking growth, readily resulting in pre-mature failure of the smart coating sensor. In some examples, the strengthening composite layer can improve the durability of the smart coating sensor.

In one example, the smart coating of the present invention further comprises a strengthening composite layer under the plurality of first sensing units. The strengthening composite layer comprises substantially continuous matrix and particles dispersed in the matrix. The particles are made of $PbTiO_3$, and the matrix is a lead-lean phase formed by lead loss of $PbTiO_3$. In another example, the particles are made of $PbZr_{0.52}Ti_{0.48}O_3$, and the matrix is a lead-lean phase formed by lead loss of $PbZr_{0.52}Ti_{0.48}O_3$.

In the prior art, it has been learned that volatilization of lead component occurs during plasma spraying using lead-containing ceramic such as lead titanate or lead zirconate titanate, hence efforts are made to reduce lead component loss in spraying process. In other words, those skilled in the art would expect avoiding lead loss in spraying of lead titanate.

Contrary to the prior art, in some examples of the present invention, a composite structured layer is formed by controlling volatilization of lead component during spraying of lead-containing ceramic powder, thereby enhancing adhesion of the lead-containing layer to a substrate, especially, durability. In one example, the strengthening composite layer comprises a substantially stoichiometric lead titanate phase and one or more lead-lean phases. The lead-lean phase may be a lead-containing phase rich in titanium dioxide or a lead-lean lead titanate ferroelectrics.

In one example, a strengthening composite layer is formed on the first insulating layer by supersonic plasma spraying process, in which the spraying powder comprises a first powder having an average particle size of D1 being about 20 μm and a second powder having an average particle size of D2 being about 5 μm, at a ratio of 4:1.

A mixed $PbTiO_3$ powder comprising the aforementioned first powder and second powder is charged to a powder feeder, adjusted to a powder feed amount of 35 g/min, and sprayed on the surface of a substrate formed with a first insulating layer at a spraying current of 350 A, a spraying voltage of 115V, a spraying power of 40.25 kW, and a spraying distance of 110 m, with argon gas at a flow rate of 3.0 $m^3/h$ as spraying main gas and hydrogen gas at a flow rate of 0.3 $m^3/h$ as secondary gas.

The above-described supersonic plasma spraying conditions enable the first powder to be melted partially, the second powder to be melted completely, and the strengthening composite layer to be formed into continuous lead-lean phase matrix and corresponding $PbTiO_3$ in the form of particles dispersed in the continuous lead-lean phase matrix.

In the example, lead titanate powder is sprayed by plasma under the conditions easy to cause lead volatilization, forming a particle phase comprising substantially stoichiometric of lead titanate, and a continuous matrix comprising lead-lean phase 1 and lead-lean phase 2 (table 1).

TABLE 1

Cross-section EDS of Pb-lean phases 1 and of a $PbTiO_3$ coating

| | Pb-lean phase 1 | | Pb-lean phase 2 | |
|---|---|---|---|---|
| Element | w/% | x/% | Element | w/% | x/% |
| O | 28.97 | 74.15 | O | 27.65 | 70.78 |
| Ti | 17.97 | 15.36 | Ti | 26.21 | 20.69 |
| Pb | 53.06 | 10.49 | Pb | 46.14 | 8.53 |
| Totals | 100.00 | 100.00 | Totals | 100.00 | 100.00 |

In a microscopic field of view, the lead-lean phase 1 presents light color regions, and the lead-lean phase 2 presents black areas. The microscopic hardness test shows that the lead-lean phase 1 has a highest hardness of 421 $HV_{0.1}$, an average hardness of 4104 $HV_{0.1}$; and the lead-lean phase 2 has a highest hardness of 540 $HV_{0.1}$ and an average hardness of 528 $HV_{0.1}$. In the regard of hardness distribution, the hardness difference between the lead-lean phase 1 and the lead-lean phase 2 rises along with increase in the distance from the substrate.

The inventor found that, by controlling the process system in plasma spraying of lead titanate, lead component loss may be very severe (so as to obtain a lead-lean phase) or very slight (so as to obtain substantially stoichiometric lead titanate). The substantially stoichiometric lead titanate (having a Pb:Ti ratio of roughly 1) and the lead-lean phase (having a Pb:Ti ratio of remarkably less than 1) are remarkably different in mechanical properties. Such property difference can notably reduce tendency of crack growth of the composite structure, so as to enhance the binding force of the coating layer and endow the lead titanate layer formed subsequently with more durable adhesion.

On the substrate formed with the strengthening composite layer, the first and second sensing units are formed by means similar to the above-described examples.

Some examples of the present invention involve formation of the first sensing units and second sensing units comprising both amorphous phase and crystalline phase. In some applications of smart coating sensors, the binding strength between the smart coating and the underlying layer will influence the detection precision of the piezoelectric sensors. In some examples of the present invention, the coating comprising both amorphous phase and crystalline phase can improve the binding force between the lead-containing coating and the underlying layer.

In one example, during the process of formation of the first sensing units and second sensing units, a circulating cooling device is employed for the substrate to be sprayed in the course of supersonic plasma spraying. The $PbTiO_3$ powder for spraying has a relatively large cooling rate during deposition onto the substrate to form a $PbTiO_3$ coating comprising both amorphous phase and crystalline phase.

In a specific example, the first sensing units are formed on the surface of the first insulating layer. Specifically, a mask having the shape of first sensing units is covered on the surface of the first insulating layer, and the $PbTiO_3$ powder granulated independently is charged into a powder feeder. The powder feed amount is adjusted to 30 g/min, and the substrate surface formed with the first insulating layer is sprayed at a spraying current of 360 A, a spraying voltage of 120V, a spraying power of 43.2 kW, and a spraying distance of 100 mm, with argon gas at a flow rate of 3.2 $m^3$/h as spraying main gas and hydrogen gas at a flow rate of 0.3 $m^3$/h as secondary gas. At the time of spraying, a liquid nitrogen loop-typed cooling device is used to perform a loop cooling to the substrate being sprayed. The condensation temperature of liquid nitrogen is −196° C., which produces a greatly large difference with the melting state powder for plasma spraying. In particular, the liquid nitrogen is directed to a pipe using a cooling system and a pressure system, passed a flow valve and connected with a huge radiator system. In front of the radiator system, there is a sample flat table for spraying. Both the face contact with the spray gun and the back face of the sample flat table for spraying are equipped with a digital temperature sensor to control the cooling rate of the samples. The substrate to be sprayed is placed onto the flat table for spraying; the substrate having a high temperature on the flat table for spraying is cooled by the radiator which absorbs the substantial heat utilizing the low temperature of liquid nitrogen, thereby achieving a large cooling rate.

The second insulating layer is formed by means similar to the above-described examples. Then, the second sensing units are formed by means similar to the first sensing units. By controlling the cooling rate of the sample, the content of the amorphous phase in the coating can be adjusted. The presence of the amorphous phase improves the binding strength between the coating and the underlying layer.

The above explanations to the disclosed examples intend to enable those skilled in the art to carry out or use the present invention. A number of modifications to these examples are obvious to those skilled in the art. The general principle defined in this application can be carried out in other examples without deviating from the concept or scope of the present invention, therefore, the invention is not limited to these examples shown in the application, but requires the broadest scope conforming to the principle and novel features disclosed in this application.

The invention claimed is:

1. A smart coating, comprising
a substrate;
a first insulating layer covering on the surface of the substrate;
a plurality of first sensing units, the plurality of first sensing units being disposed on the surface of the first insulating layer and arranged in a second direction, and the first sensing units extending in a first direction;
a second insulating layer covering on the surfaces of the plurality of first sensing units and the first insulating layer;
a plurality of second sensing units, the plurality of second sensing units being disposed on the surface of the second insulating layer and arranged in the first direction, and the second sensing units extending in the second direction; and
a wear-resistant layer covering on the surfaces of the second sensing units and the second insulating layer;
wherein the plurality of first sensing units and the plurality of second sensing units have piezoelectric effect,
and wherein the wear-resistant layer is a FeCrBSi layer.

2. The smart coating according to claim 1, wherein the first direction is perpendicular to the second direction.

3. The smart coating according to claim 1, further comprising a strengthening composite layer under the plurality of first sensing units.

4. The smart coating according to claim 3, wherein the strengthening composite layer comprises substantially continuous matrix and particles dispersed in the matrix.

5. The smart coating according to claim 4, wherein the particles are made of PbTiO3, and the matrix is a lead-lean phase formed by lead loss of PbTiO3; or the particles are made of PbZr0.52Ti0.48O3, and the matrix is a lead-lean phase formed by lead loss of PbZr0.52Ti0.48O3.

6. The smart coating according to claim 1, wherein the distance between two adjacent first sensing units and the distance between two adjacent second sensing units are both 2 mm to 4 mm.

7. The smart coating according to claim 1, wherein the first insulating layer and the second insulating layer are both constituted by an aluminum oxide layer or a titanium oxide layer or a composite layer of aluminum oxide and titanium oxide.

8. The smart coating according to claim 1, wherein the materials for manufacturing the first sensing unit and the second sensing unit are independently selected from PbTiO3 or PbZr0.52Ti0.48O3.

9. The smart coating according to claim 1, further comprising
a first upper electrode disposed on the edge of the upper surface of the first sensing units;
a first lower electrode disposed on the edge of the lower surface of the first sensing units;
a second upper electrode disposed on the surface of the second sensing units; and
a second lower electrode disposed on the edge of the lower surface of the second sensing units.

10. A locating method based on the smart coating of claim 1, comprising:
when the wear-resistant layer is worn, the first sensing units generate first detection signals, and the second senor units generate second detection signals;
screening the first detection signals and second detection signals, and selecting the maximum first detection signal and the maximum second detection signal;
locating the damaged position in the second direction of the wear-resistant layer by the first sensing unit that generates the maximum first detection signal;
locating the damaged position in the first direction of the wear-resistant layer by the second sensing unit that generates the maximum second detection signal; and determining the damaged position of the wear-resistant layer through the damaged positions in the first direction and second directions of the wear-resistant layer.

11. A method for manufacturing the smart coating, comprising
forming a first insulating layer on a substrate;
forming a plurality of first sensing units on the surface of the first insulating layer, the plurality of first sensing units being arranged in a second direction, and the first sensing units extending in a first direction;
forming a second insulating layer on the surfaces of the plurality of first sensing units and the first insulating layer;
forming a plurality of second sensing units on the surface of the second insulating layer, the plurality of second sensing units being arranged in the first direction, and the second sensing units extending in the second direction;
forming a wear-resistant layer on the surfaces of the second sensing units and the second insulating layer; and
polarizing the first sensing units and second sensing units to impart piezoelectric effect to the first sensing units and second sensing units,
and wherein the wear-resistant layer is a FeCrBSi layer.

12. The method according to claim 11, wherein forming a first insulating layer on the surface of a substrate comprises:
forming a first insulating layer on the surface of the substrate by supersonic plasma spraying process.

13. The method according to claim 11, wherein forming a second insulating layer on the surfaces of the plurality of first sensing units and the first insulating layer comprises:
forming a second insulating layer on the surfaces of the plurality of first sensing units and the first insulating layer by supersonic plasma spraying process.

14. The method according to claim 11, wherein forming a plurality of first sensing units on the surface of the first insulating layer comprises:
covering a mask having the shape of the plurality of first sensing units on the surface of the first insulating layer; and
forming the plurality of first sensing units on the surface of the first insulating layer by supersonic plasma spraying process.

15. The method according to claim 11, wherein forming a plurality of second sensing units on the surface of the second insulating layer comprises:
covering a mask having the shape of the plurality of second sensing units on the surface of the second insulating layer; and
forming a plurality of second sensing units on the surface of the second insulating layer by supersonic plasma spraying process.

16. The method according to claim 11, wherein forming a wear-resistant layer on the surfaces of the second sensing units and second insulating layer comprises:
forming a wear-resistant layer on the surfaces of the second sensing units and second insulating layer by supersonic plasma spraying process.

17. The method according to claim 11, further comprising
forming a first upper electrode on the edge of the upper surface of the first sensing units;
forming a first lower electrode on the edge of the lower surface of the first sensing units;
forming a second upper electrode on the surface of the second sensing units;
forming a second lower electrode on the edge of the lower surface of the second sensing units; and
drying.

18. The method according to claim 11, further comprising
forming a strengthening composite layer on the substrate and the first insulating layer by supersonic plasma spraying process.

19. The method according to claim 18, wherein in the process of forming the strengthening composite layer by supersonic plasma spraying, the powder used for spraying comprises a first powder having an average particle size of D1 and a second powder having an average particle size of D2 with a ratio of D1 to D2 varying from 2 to 6, and the supersonic plasma spraying conditions are selected such that the first powder is melted completely and the second powder is melted partially.

20. The method according to claim 19, wherein the first powder and the second powder are PbTiO3 or PbZr0.52Ti0.48O3, respectively, and the strengthening composite layer is composed of a matrix of continuous lead-lean phase and corresponding PbTiO3 or PbZr0.52Ti0.48O3 in particle form dispersed the matrix of continuous lead-lean phase.

* * * * *